United States Patent [19]

Laker

[11] 4,175,439

[45] Nov. 27, 1979

[54] APPARATUS AND METHOD FOR COLLECTING, STORAGE AND TRANSPORTING LIQUID SAMPLES FOR DIAGNOSTIC EXAMINATION

[76] Inventor: Thomas L. Laker, 760-A Green Hill Rd., Madison, Conn. 06443

[21] Appl. No.: 797,512

[22] Filed: May 13, 1977

[51] Int. Cl.² .......... G01N 1/12

[52] U.S. Cl. .......... 73/425.4 R; 128/269

[58] Field of Search .......... 73/425, 425.4; 128/2 F, 128/2 W, 269; 150/3

[56] References Cited

U.S. PATENT DOCUMENTS

| | | | |
|---|---|---|---|
| 2,591,927 | 4/1952 | Gladstone | 128/269 |
| 2,902,146 | 9/1959 | Doherty | 73/425 |
| 3,282,114 | 11/1966 | Pell | 73/425 |
| 3,395,788 | 8/1968 | Gill | 150/3 |

*Primary Examiner*—S. Clement Swisher
*Attorney, Agent, or Firm*—Roy L. Parsell

[57] ABSTRACT

Apparatus for collecting, storage and transporting liquid samples for industrial and diagnostic purposes consisting of a pliable liquid absorbent member manipulated by a handling stick for transferring the absorbent member containing the liquid sample into a sealable pouch having a flexible transparent wall and after removing the handling stick sealing the container for storage and transporting to a testing laboratory.

3 Claims, 6 Drawing Figures

12

14

15

13

16

11

10
11

10
11

12

12
11

14
15
13
16

12
14
15
13
16
11

APPARATUS AND METHOD FOR COLLECTING, STORAGE AND TRANSPORTING LIQUID SAMPLES FOR DIAGNOSTIC EXAMINATION

BACKGROUND OF THE INVENTION

1. Field of the Invention

This invention relates to new and useful improvements in apparatus and methods for collecting, containing, storage and transporting liquid samples for industrial and diagnostic examination.

2. Description of the Prior Art

In certain industrial processes and products fluids may be present in various degrees of concentration and requiring sampling for analysis to insure against damage during process and to maintain standards of quality of the product.

Samples of the liquids are taken from the process underway or in storage or as the case may be of the raw materials to be subsequently used in the final product as well as the final product. The usual procedure is to procure a sample in a container and transport it to the testing laboratory, taking necessary steps to protect the quality of the sample as procured.

In a similar manner certain body fluids require examination and fluid samples must be procured and transported to the appropriate laboratory and examination. The procedure as applied to human beings and animals presents additional special problems.

The apparatus and method of the present disclosure is especially useful in the case of veterinary medicine.

SUMMARY

The invention comprises an improvement in procuring the samples of urine, storage and transporting to testing laboratories. The devices and procedure are particularly adaptable to veterinarians but obviously are also adaptable to human beings.

DESCRIPTION OF THE PREFERRED EMBODIMENT

Figures 1, 2, 3, 4, 5, 6:
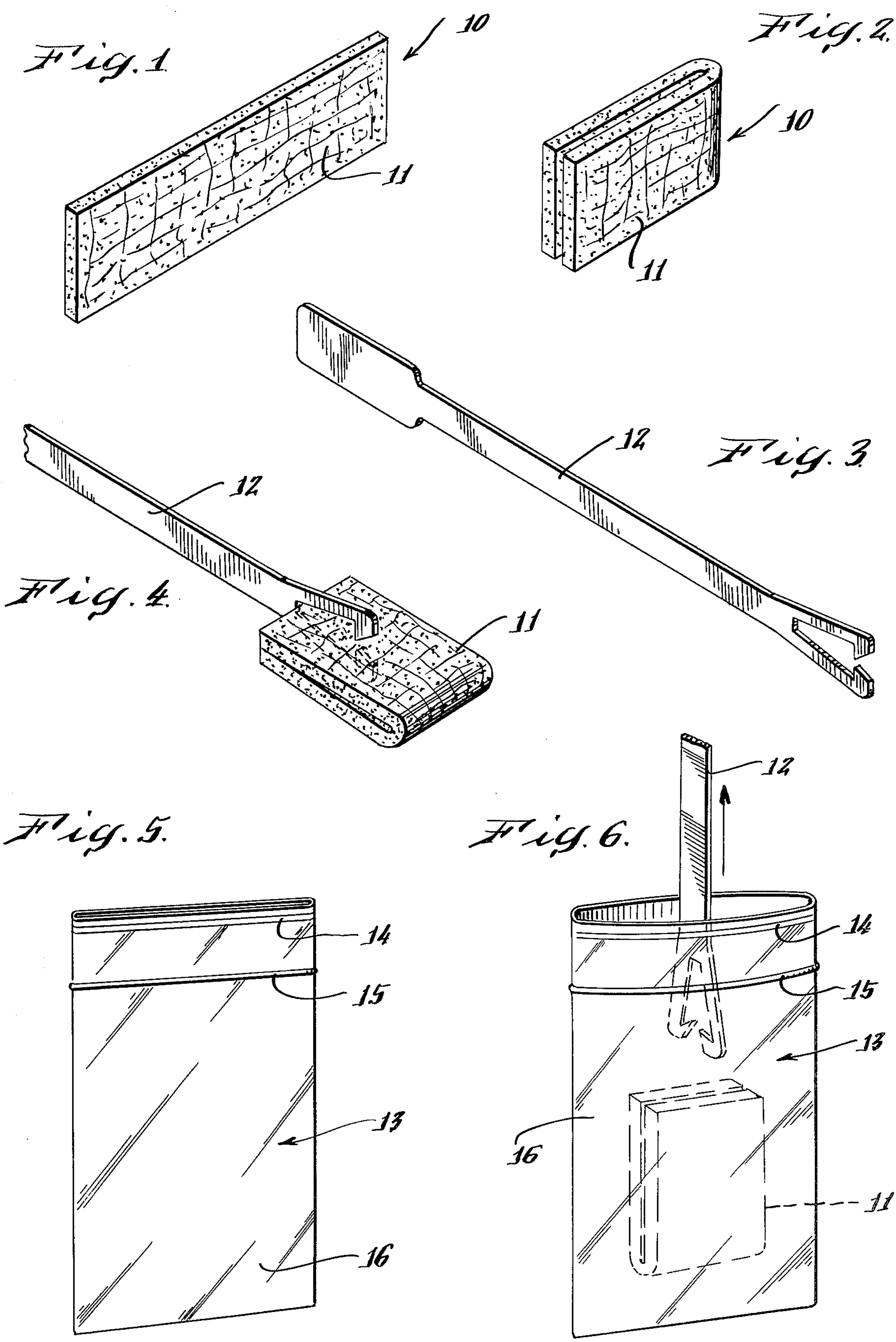
FIG. 1 is a perspective view of the resilient absorbent member to hold the sample.
FIG. 2 is a perspective view of the absorbent member formed into position to be inserted in the handling stick.
FIG. 3 is a perspective view of the handling stick.
FIG. 4 is a perspective view of the absorbent member mounted in the handling stick.
FIG. 5 is a vertical perspective side view of the container in a closed position.
FIG. 6 is a vertical perspective view of the container with the handling stick removed from the absorbent member but still in the container.

For purposes of best describing the device, its application to the veterinary profession is selected as an example but this device is in no way limited to such application.

The sample collecting member 11 is of resilient absorbent material having a capillary structure to absorb a desired portion of the liquid desired for sampling when placed in contact therewith. The resilience of the material of the member 11 combined with the fold help to hold the absorbent member 11 between the tines of the handling stick. The tines may also have resilience. The folding of the absorbent member 11 also enables more surface to be presented for collecting a urine sample.

With the absorbent member mounted into the handling stick 12, it is more convenient to obtain a specimen of urine directly from the discharge stream of the animal as compared to collection by means of an open dish or container.

The container 13 is preferably a flat flexible plastic pouch having clear side walls and open at one end which permits closing and sealing.

The preferred sealing means comprises a groove 15 in one half side of the container inner wall 16 and a companion bead (not shown) in the opposite half of the container inner wall 16 which when both are pressed together hold the sides tightly together so that no moisture can exit or enter through the thus sealed end of the container.

The empty container as received is flat and closed. One side is provided with a guideline 14 of distinguishing mark or color and the portion of the side opposite the guideline 14 is blank. The veterinarian or the client is thus assisted in grasping each respective side and pulling the sides apart to open the container. To seal the container pressure is applied to each side wall of the container to force the bead 15 into its companion groove (not shown) where it is held securely by the resilience of the container wall material.

After the specimen of urine has been absorbed from the stream into the absorbent material 11 by the veterinarian or person taking the sample, the handling stick 12 with the absorbent member 11 thereon are inserted into the container 13.

Then by holding the absorbent member 11 by pressing the walls of the container 13 against member 11 the handling stick may be withdrawn and the container 13 closed and sealed as previously described.

The sample is now ready to be transferred to the testing laboratory for examination.

While it is important to make examination as soon as possible, if it is not so convenient, the container may be stored in a refrigerator since it is not only sealed but there is very little free liquid since virtually all of it remains in the absorbent members 11 until expressed.

When the container 13 containing the sample is ready for examination, the container 13 may be opened as previously described and some of the sample forced out by squeezing the walls of the container against the absorbent member thereby forcing out some of the sample which can be then poured from the container.

Alternatively after opening the container 13 some of the sample may be squeezed from the absorbent member but still remaining in the container and a strip containing deposits of different reagents inserted into the container 13 and the reactions observed or prescribed by the manufacturers of such reagent containing strips.

Having described my invention, I claim:

1. A device for collecting, storage, transporting and discharging a liquid sample collected from a liquid supply desired to be examined for medical, industrial or diagnostic purposes comprising (a) a resilient absorbent member having sufficient capillary structure to absorb a portion of the liquid to be sampled when the absorbent member is placed in contact with the liquid supply or when the member is removed from the liquid supply to discharge the absorbed liquid upon the application of compressive pressure to the absorbent member;

(b) a sealable container for receiving, containing, storage and transporting the absorbent member holding the liquid;

(c) a handling stick for removably attaching the absorbent member thereto for inserting and removing the absorbent member relative to the liquid supply and the container respectively;

(d) the handling stick is provided at one end with a fork portion having tines for holding the absorbent member.

2. The device according to claim 1 wherein one of the tines is provided with a barb for releasably gripping the absorbent member.

3. A device for collecting, storage, transporting and discharging a liquid sample collected from a liquid supply to be examined for medical, industrial or diagnostic purposes comprising (a) a resilient absorbent member having sufficient capillary structure to absorb a portion of the liquid to be sampled when the absorbent member is placed in contact with the liquid supply or when the member is removed from the liquid supply to discharge the absorbed liquid upon application of compressive pressure to the absorbent member;

(b) a sealable container for receiving, containing, storage and transporting the absorbent member holding the liquid sample; and (c) an elongated handling member having a slotted end to receive and removably hold the absorbent member for collecting the liquid sample and depositing the absorbent member containing the sample into the container.

* * * * *